(12) United States Patent
Tapocik

(10) Patent No.: US 9,277,975 B1
(45) Date of Patent: Mar. 8, 2016

(54) INTERPROXIMAL DENTAL TOOL WITH STRAIGHT AND CURVED BLADE INCLUDING IMPROVED GRIPPING UPPER AND SIDE SURFACES AND SAFETY RETAINING MEMBERS

(71) Applicant: Kerr Corporation, Orange, CA (US)

(72) Inventor: Bryan Tapocik, Highland, CA (US)

(73) Assignee: Kerr Corporation, Orange, CA (US)

( * ) Notice: Subject to any disclaimer, the term of this patent is extended or adjusted under 35 U.S.C. 154(b) by 0 days.

(21) Appl. No.: 14/523,910

(22) Filed: Oct. 26, 2014

(51) Int. Cl.
*A61C 15/00* (2006.01)
*A61C 3/12* (2006.01)
*A61C 5/12* (2006.01)
*A61C 3/06* (2006.01)

(52) U.S. Cl.
CPC . *A61C 15/00* (2013.01); *A61C 3/12* (2013.01); *A61C 3/06* (2013.01); *A61C 5/125* (2013.01)

(58) Field of Classification Search
CPC .......... A61C 1/00; A61C 1/0053; A61C 1/10; A61C 1/12; A61C 1/14; A61C 3/06; A61C 3/12; A61C 3/00; A61C 3/04; A61C 5/125; A61C 5/127; A61C 15/00; B26B 19/3853; B26B 19/3846; B26B 21/52; B26B 21/521; B26B 21/522; B26B 21/525; B26B 21/527; B26B 21/565; B26B 27/00; B26B 27/005; B26B 27/007; A61D 5/00; A61B 17/14; B23D 67/12; B23D 71/04
USPC .............. 132/329, 321, 213, 213.1, 214, 215, 132/323; 433/51, 114, 125, 142, 144, 134, 433/166, 143, 46, 148, 149, 39, 40, 141; D24/152, 147, 176; 30/30, 32, 34.05, 30/314, 526, 537, 295, 51; 606/82; D8/90
See application file for complete search history.

(56) References Cited

U.S. PATENT DOCUMENTS

| | | | | |
|---|---|---|---|---|
| 615,316 | A * | 12/1898 | Snedaker | 433/144 |
| 1,174,932 | A * | 3/1916 | Grenier | 30/51 |
| 1,201,875 | A * | 10/1916 | Russ | 433/142 |
| 2,288,011 | A * | 6/1942 | Mizzy | 433/148 |
| 2,730,804 | A * | 1/1956 | Saupe | 433/142 |
| 2,752,682 | A * | 7/1956 | Wiseman | 433/127 |
| 4,299,572 | A * | 11/1981 | McKinney | 433/144 |
| 4,483,676 | A * | 11/1984 | Thierman | 433/142 |
| 4,592,729 | A * | 6/1986 | Bilciurescu | 433/142 |
| 5,084,978 | A * | 2/1992 | McReynolds | 30/517 |
| 5,476,381 | A * | 12/1995 | Dragan | 433/142 |
| 5,908,036 | A * | 6/1999 | Andrews | 132/215 |
| 6,267,117 | B1 * | 7/2001 | Bisson | 132/200 |
| 6,473,971 | B2 * | 11/2002 | Ordaz | 30/47 |

(Continued)

*Primary Examiner* — Vanitha Elgart
(74) *Attorney, Agent, or Firm* — Wood, Herron & Evans, LLP

(57) ABSTRACT

An interproximal dental tool for use by dental practitioners which contains several significant improvements over prior art interproximal dental tools which has an upper surface extending to a sidewall and a body section which in turn grasps a razor or blade member having a blade extending outwardly from the interproximal dental tool and which is placed between the patient's teeth to grind portions of teeth between two adjacent teeth. The tool is used for professional practice only and not by consumers. The significant improvements over the prior art interproximal dental tools are as follows: The exterior top surface and the exterior side surfaces of the present invention interproximal dental tool are made of grippable material which is primarily made of rubber.

14 Claims, 9 Drawing Sheets

(56) References Cited

U.S. PATENT DOCUMENTS

| | | | |
|---|---|---|---|
| 6,925,719 B2 * | 8/2005 | Callne | 30/392 |
| 7,322,822 B2 * | 1/2008 | Navarro | 433/125 |
| 7,455,521 B2 * | 11/2008 | Fishburne, Jr. | 433/142 |
| D600,810 S | 9/2009 | Khouri | |
| D609,341 S | 2/2010 | Khouri | |
| 7,698,823 B1 * | 4/2010 | Iadarola | 30/537 |
| 7,758,343 B1 * | 7/2010 | Navarro | 433/142 |
| 7,914,284 B2 * | 3/2011 | Kim | 433/142 |
| D638,127 S | 5/2011 | Khouri | |
| 8,506,295 B2 * | 8/2013 | Rek | 433/166 |
| 8,535,057 B2 * | 9/2013 | Kim | 433/142 |
| 8,932,057 B2 * | 1/2015 | Kim | 433/142 |
| 2006/0063131 A1 * | 3/2006 | Kim | 433/142 |
| 2006/0127845 A1 | 6/2006 | Khouri | |
| 2007/0089578 A1 * | 4/2007 | Zoot | 83/13 |
| 2010/0297575 A1 * | 11/2010 | Effenberger et al. | 433/87 |
| 2012/0192427 A1 * | 8/2012 | Hazard | 30/30 |
| 2012/0258425 A1 * | 10/2012 | Rek | 433/142 |

\* cited by examiner

INTERPROXIMAL DENTAL TOOL WITH STRAIGHT AND CURVED BLADE INCLUDING IMPROVED GRIPPING UPPER AND SIDE SURFACES AND SAFETY RETAINING MEMBERS

BACKGROUND OF THE INVENTION

1. Field of the Invention

The present invention relates to the field of dental hygiene and in particular, an interproximal dental tool which is used to clean plaque and to also grind tooth structures at locations between two adjacent teeth. This interproximal dental tool is for professional use by a dentist only and is not for consumer use.

2. Description of the Prior Art

The following four patents and published patent applications are the closest prior art known to the inventor.

1. United States Patent Publication No. 2006/0127845 by inventor Louie Khouri for "INTERPROXIMAL DENTAL TOOL" published on Jun. 15, 2006.

2. U.S. Design Pat. No. D600,810 issued on Sep. 22, 2009 to Khouri for "INTERPROXIMAL DENTAL TOOL".

3. U.S. Design Pat. No. D609,341 issued on Feb. 2, 2010 to Khouri for "INTERPROXIMAL DENTAL TOOL".

4. U.S. Design Pat. No. D638,127 issued on May 17, 2011 to Khouri for "INTERPROXIMAL DENTAL TOOL".

These are variations on interproximal dental tools which have certain defects that have been noted by the present inventor and there is a significant need for an improvement over the prior art interproximal dental tools.

SUMMARY OF THE INVENTION

The present invention is an interproximal dental tool which contains several significant improvements over prior art interproximal dental tools which has an upper surface extending to sidewall and a body section which in turn grasps a razorblade or blade member having a blade extending outwardly from the interproximal dental tool and which is placed between the patient's teeth to grind portions of teeth between two adjacent teeth. The tool is used for professional practice only and not by consumers.

The present invention has several significant improvements over the prior art interproximal dental tools which are as follows: (1) The top surface and the side surface of the present invention interproximal dental tool have an upper surface and side surfaces which are made of grippable material selected from the group consisting of rubber and polyvinyl chloride.

In addition to the upper surface and sidewalls being made of grippable material, each sidewall has protruding gripping members such as protrusions extending from the sidewall which makes the interproximal dental tool easier to grasp. Therefore, the combination of the grippable material on the upper surface and sidewalls combined with the extending protrusions on the sidewalls enables a practitioner to grasp the interproximal dental tool at the location of both sidewalls and the protruding members and retain the interproximal dental tool between two of the practitioner's fingers, one of the fingers being the thumb and the second finger almost always being the forefinger although in theory, the middle finger could also be used in place of the forefinger.

An additional improvement is to have a retaining member affixed to the interproximal dental tool, which retaining member extends around at least the practitioner's wrist and preferably also a portion of the professional's fingers so that should the interproximal dental tool slip out of the practitioner' hands, it will not fall down the patient's throat but instead, can be pulled quickly out of the patient's mouth or alternatively, will dangle below the practitioner's wrist and fingers in the event it does not fall into the patient's mouth. Either way, it prevents the interproximal dental tool from falling down the patient's throat, potentially creating serious injury to the patient.

The interproximal dental tool consists of two variations. The first is a straight design which basically has all of the components in a straight configuration including the razorblade. The second variation is an arcuate design where the components are arcuate in shape and the blade is arcuate in shape as well with an arcuate sharp edge.

The components of the interproximal dental tool consist of the top surface extending to a left and right side surface having protrusions respectively extending out of right and left surfaces and a body section which can include a first section adjacent the upper wall, a middle section between the rim section adjacent the upper wall and sidewalls and a main body section extending throughout the entire area of the interproximal dental tool and having a slot which permanently retains a razorblade which has a razorblade edge extending therefrom which is inserted between the patient's teeth.

One variation is to have a straight design where all the components are straight and the second variation is essentially the same as the first variation but the design is arcuate in shape including an arcuate top and arcuate body and an arcuate blade.

Either variation has a pair of openings extending through the upper body section and a retaining member such as a strap extends through the two openings and is either tied and affixed at the location of the two openings or preferably at a remote location or alternatively after the retaining members are extending through the openings, the retaining member is soldered or otherwise formed shut so that it is a one-piece retaining member which can be retained around the practitioner's fingers and wrist so that as the practitioner grasps the interproximal dental tool on the two opposite sidewalls and protrusions between two fingers, primarily the practitioner's thumb and forefinger and uses the razor edge to grind between two teeth, the retaining member will retain the interproximal dental tool in the event it slips out of the practitioner's hands.

It is therefore an object of the present invention to create an improved interproximal dental tool which has an improved gripping member on its sidewalls and top which enable the practitioner to more securely grip the interproximal dental tool when it is in use.

It is a further object of the present invention to provide further gripping mechanisms such as protrusions on the sidewall to assist in the gripping of the interproximal dental tool during operation.

It is still a further object of the present invention to provide a retaining member which will retain the interproximal dental tool should it fall out of the practitioner's hand so that the interproximal dental tool will not fall down a patient's throat.

Further novel features and other objects of the present invention will become apparent from the following detailed description, discussion and the appended claims, taken in conjunction with the drawings.

BRIEF DESCRIPTION OF THE DRAWINGS

Referring particularly to the drawings for the purpose of illustration only and not limitation, there is illustrated.

Figure 1:
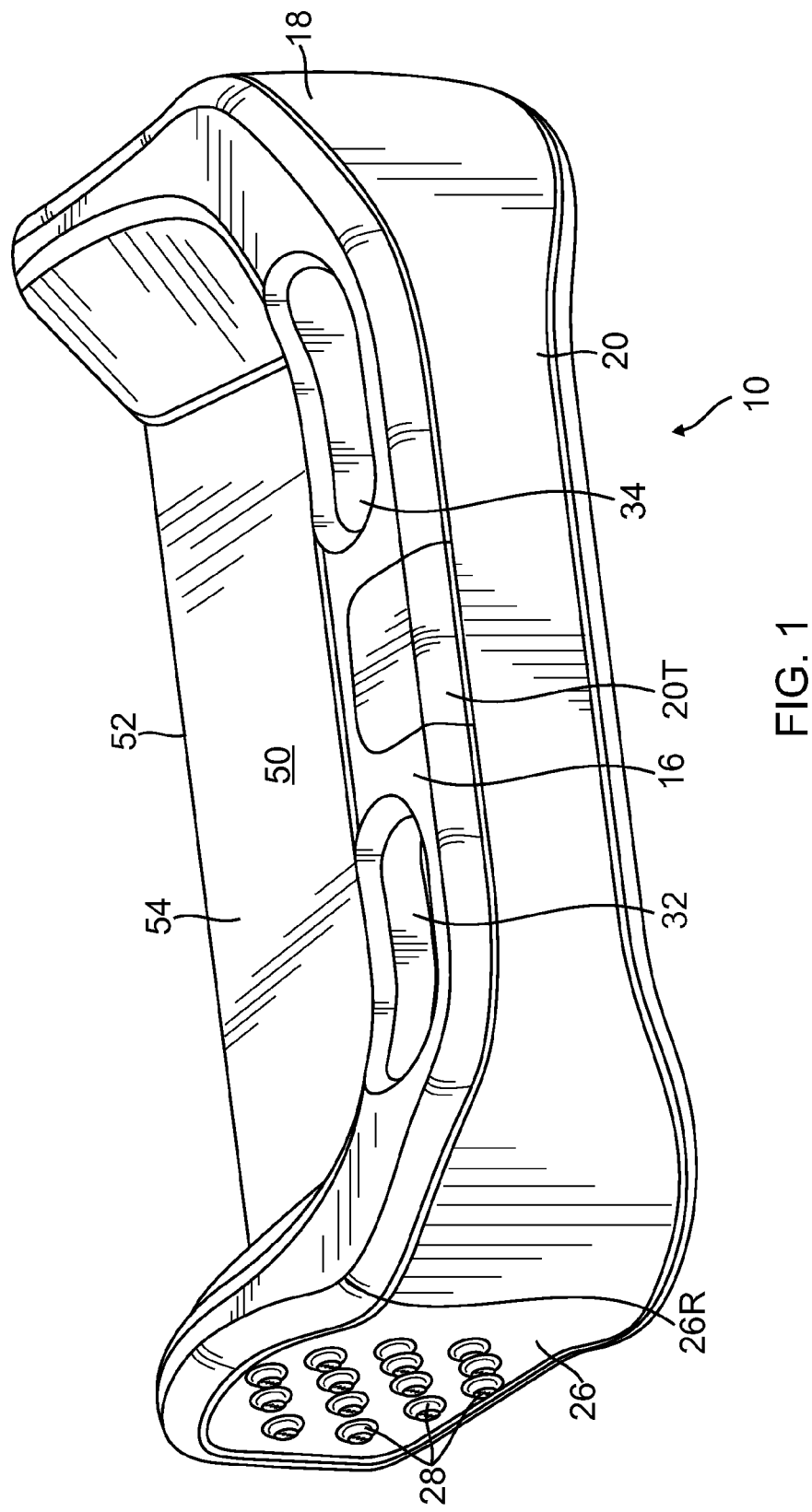
FIG. 1 is a top front side perspective view of the interproximal dental tool.
Figure 2:
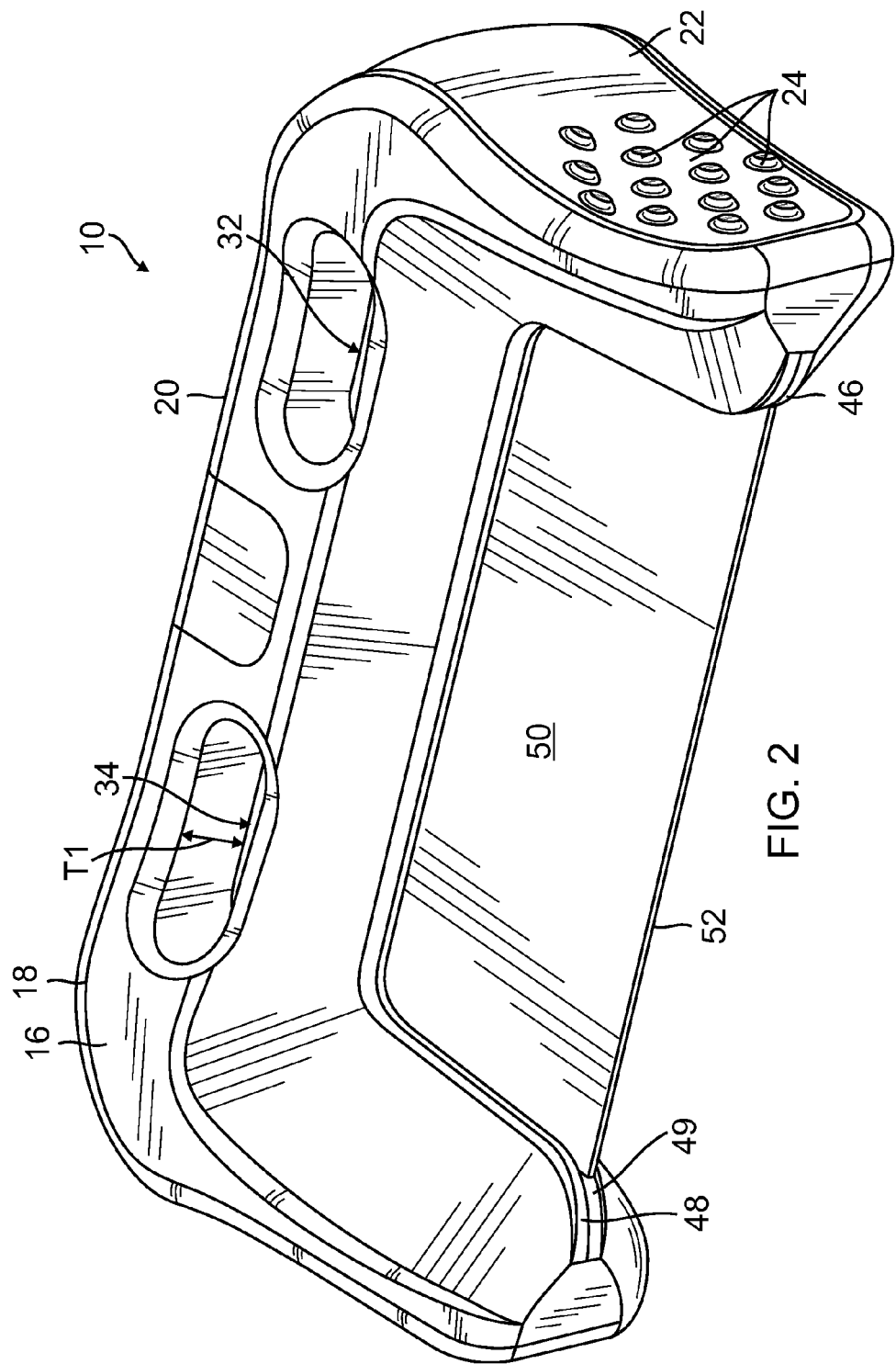
FIG. 2 is a bottom rear side perspective view thereof.
Figure 3:
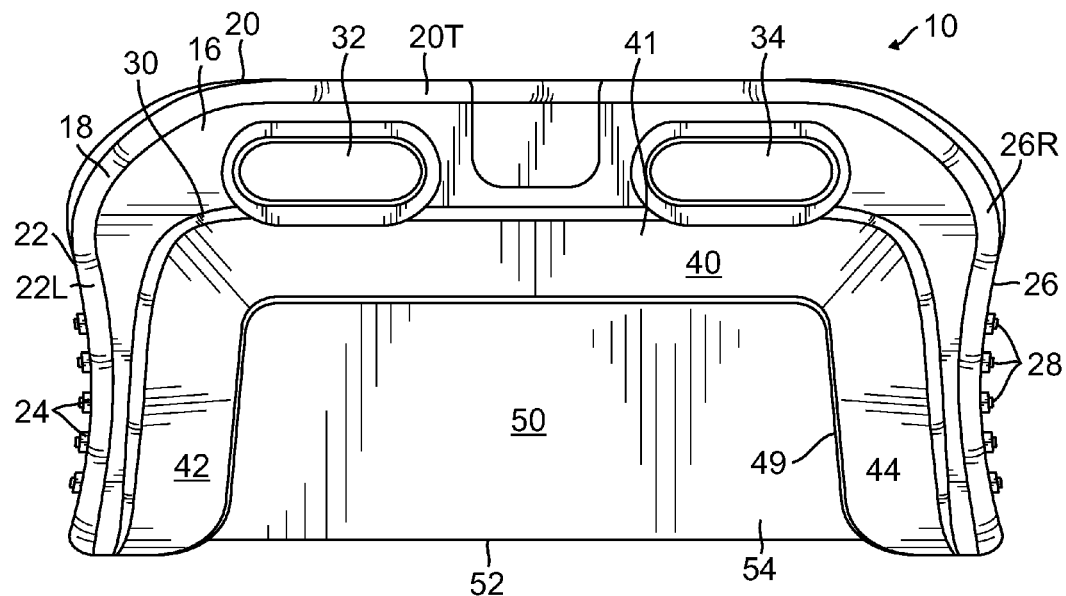
FIG. 3 is a front elevational view thereof.
Figure 4:
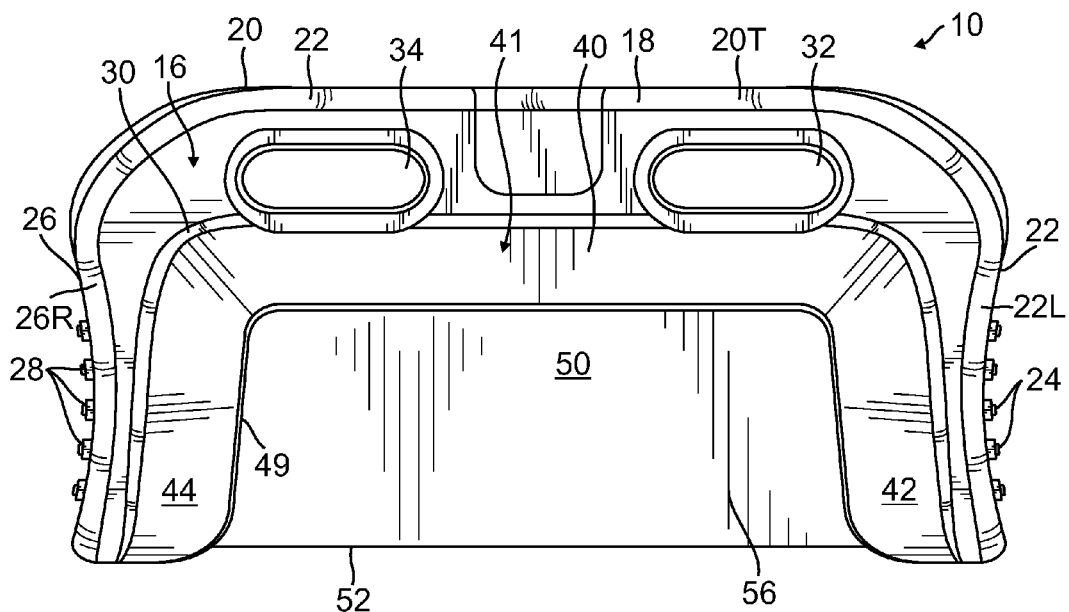
FIG. 4 is a rear elevational view thereof.
Figure 5:
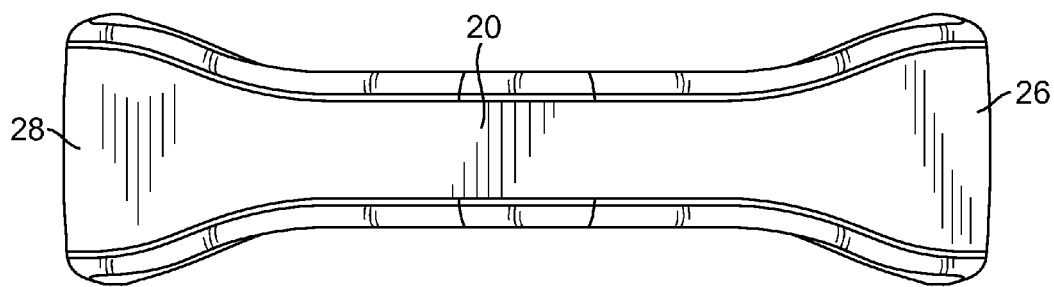
FIG. 5 is a top plan view of one embodiment of the present invention interproximal dental tool which is a straight blade.
Figure 6:
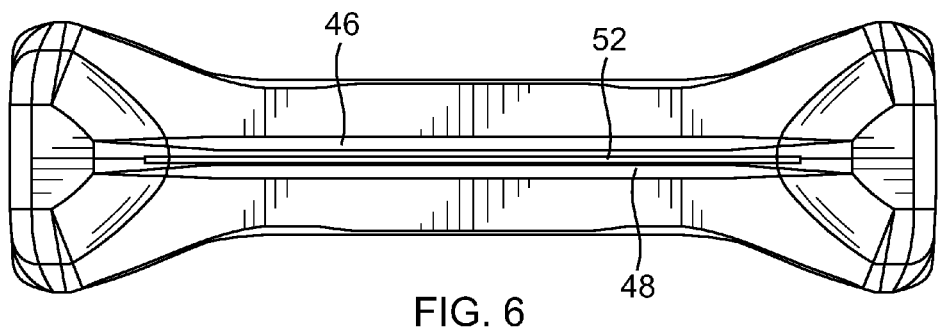
FIG. 6 is a bottom plan view thereof.
Figure 7:
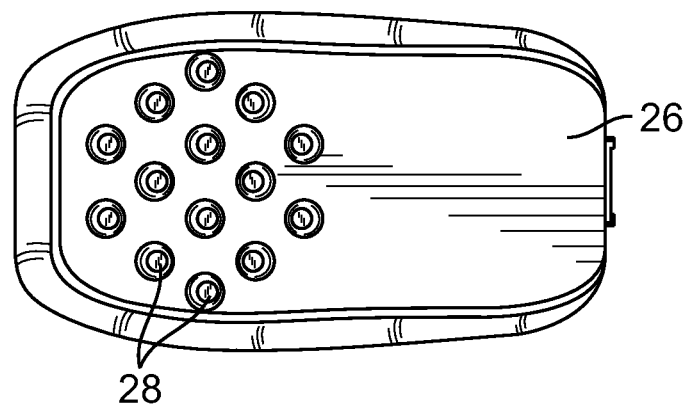
FIG. 7 is a left side view thereof.
Figure 8:
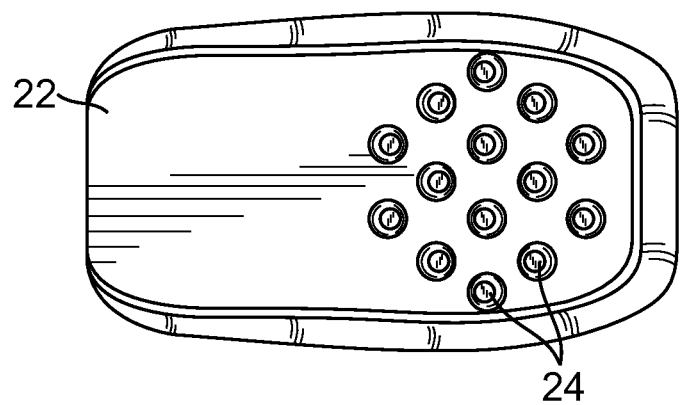
FIG. 8 is a right side view thereof.

DETAILED DESCRIPTION OF EMBODIMENTS OF THE PRESENT INVENTION ILLUSTRATING THE BEST EMBODIMENTS KNOWN TO THE INVENTOR AT THE TIME THE APPLICATION WAS FILED

Although specific embodiments of the present invention will now be described with reference to the drawings, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope and contemplation of the present invention as further defined in the appended claims.

Referring to FIGS. 1, 2, 3 and 4, there is illustrated the key components of the base invention of the interproximal dental tool with a first embodiment having straight blade design. The interproximal dental tool 10 has an exterior top surface 20 extending to an exterior left side surface 22 and to an exterior right side surface 26.

A key innovation of the present invention is that the top exterior surface 20 and its exterior side surfaces 22 and 26 are made of rubber such as thermoplastic polyurethane elastomer (TPE) and therefore, are easier to grip for a dental practitioner such as a dentist or dental hygienist. In prior art interproximal dental tools, the top is made of plastic or similar more slippery material which is more difficult to grip and results in the dental hygienist or dentist frequently losing control of the device since the device is used as an apparatus to grind locations between two teeth of the human being where there is frequently saliva and other slippery materials within the human being's mouth.

in addition to the innovation of having an exterior soft grippable top 20 extending to exterior soft grippable sidewalls 22 and 26 which are easy to grip, a second innovation of the present invention is having a multiplicity of gripping members such as extending protrusions on the exterior sidewalls of the interproximal dental tool 10. The protrusions are shown as 24 on the exterior left sidewall 22 and are shown as protrusions 28 on the exterior right sidewall 26. The protrusions combined with the soft grippable side and upper surfaces of the interproximal dental tool 10 make the interproximal dental tool far more easy to grip than the prior art interproximal dental tools which are typically made of plastic or other hard material which is more difficult to grip.

The exterior top surface 20 is above a top horizontal wall 20T. The left exterior side surface 22 extends from a left sidewall 22L. The right exterior side surface 26 extends from a right sidewall 26R.

Top wall 20T, left sidewall 22L and right sidewall 26R when combined serve as an exterior rim 18 which is adjacent the exterior upper surface 20 and exterior sidewalls 22 and 26 and extends to the entire length of the upper surface and both sidewalls.

Beneath the rim 18 is the main body section 16 which extends interiorly of the rim 18 and includes two elongated openings 32 and 34 which extend through the entire thickness T1 of the interior body section 16 of the interproximal dental tool. The interproximal dental tool 10 further comprises a main razorblade retaining body section 40 having an interior horizontal wall 41, a left interior sidewall 42 and a right interior sidewall 44. A circumferential slot 49 extends for the entire distance of the interior of the razor retaining body 40 and the horizontal wall 41 and sidewalls 44 and 42. The razor retaining slot 49 is bounded by front circumferential wall 46 and a rear circumferential wall 48, each of which extend for the entire circumferential distance of slot 49. Inserted and retained within the slot 49 between front circumferential wall 46 and rear circumferential wall 48 is a straight razorblade 50 having a front surface 54, a rear surface 56 and a bottom sharp edge 52 which is the portion of the interproximal dental tool 10 that is used to grind the location between teeth.

Figure 11:
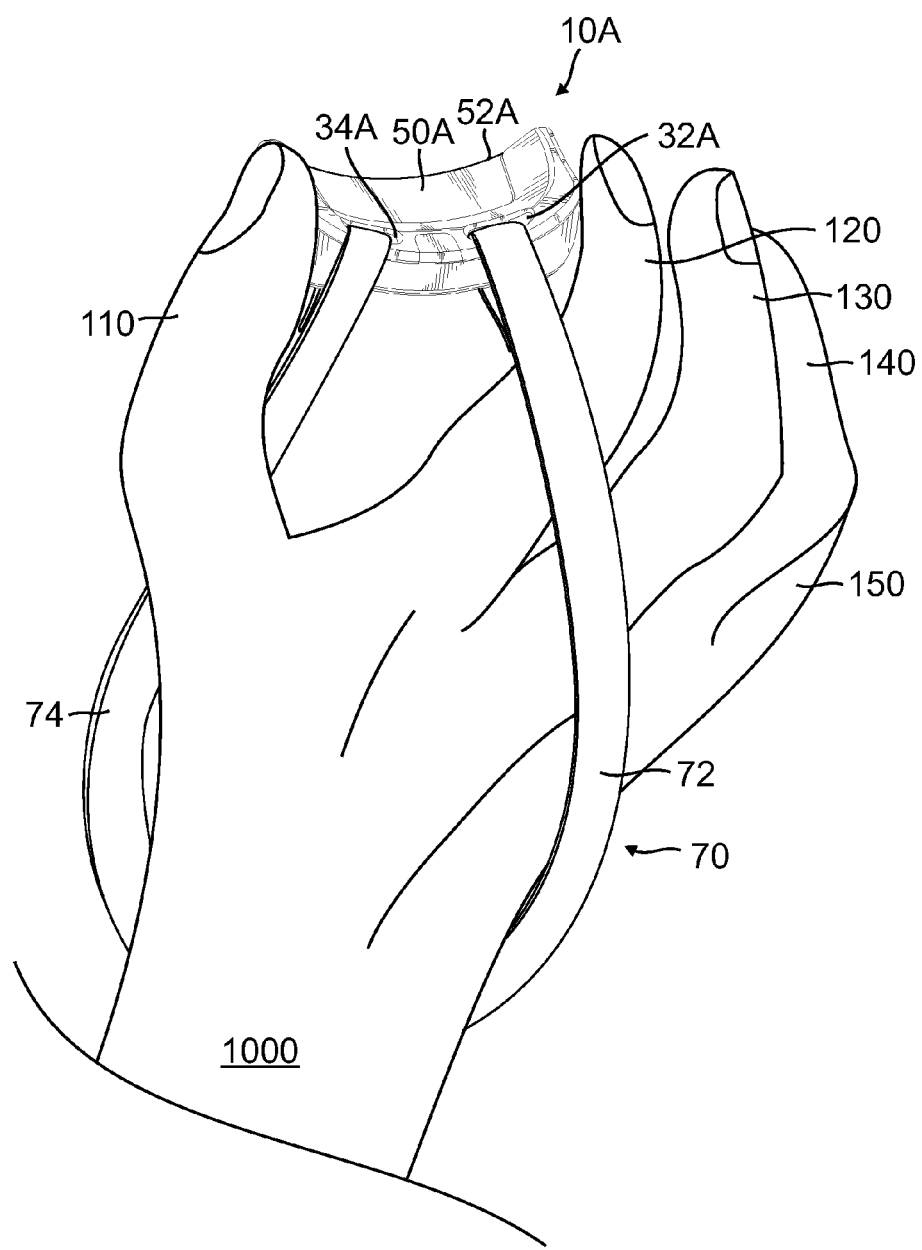
FIG. 11 is a perspective view of a second embodiment of the present invention having an arcuate blade for the interproximal dental tool being held by a dentist or dental hygienist with a safety strap.
Figure 12:
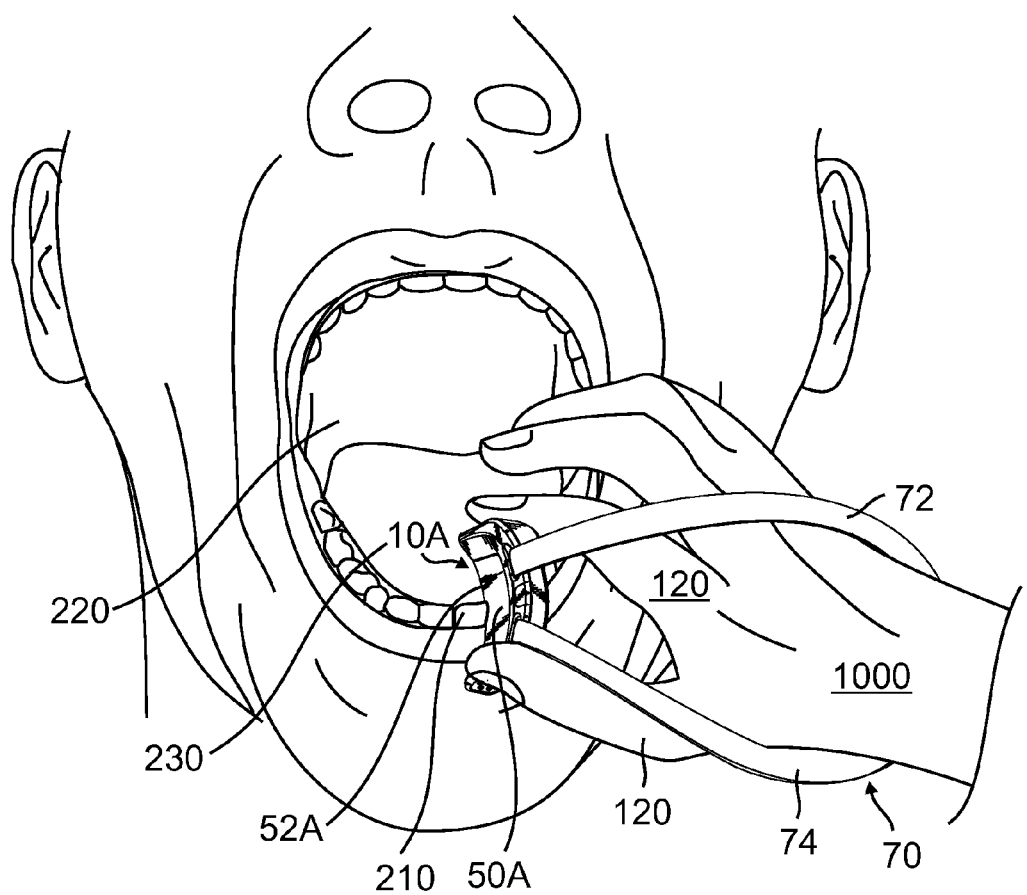
FIG. 12 is a perspective view of the second embodiment of the present invention inserted between two teeth of a patient and the safety strap wrapped around the hand of the dentist or dental hygienist while the interproximal dental tool is being used.

The specific embodiment of the invention illustrated in FIGS. 1-10 is a first embodiment where the blade is a straight blade. An alternative embodiment of the present invention which is illustrated in FIGS. 11 and 12 is an arcuate blade design. The components of the arcuate interproximal dental tool are the same as the components of the straight interproximal dental tool but have an arcuate bend to them. Therefore, a key innovation of the present invention is the incorporation of a grippable arcuate upper surface and arcuate sidewalls which include protrusions which make the interproximal dental tool much easier to grip between the fingers of a dental practitioner than prior art interproximal dental tools which are made of harder material such as plastic which is more difficult to grip, especially in an environment where there is a lot of mucus, saliva and other fluids that a person emits while undergoing a dental procedure. The razorblade front surface 50A is also arcuate.

As described above, also illustrated in FIG. 9 is the hand 1000 where primarily the thumb 110 and forefinger 120 respectively grip the sidewalls 22 and 26 and protrusions of the interproximal dental tool 10 with the bottom sham edge 52 of the razorblade 50 facing away from the area that is gripped.

One problem that occurs with use of an interproximal dental tool which is not widely publicized is that as a dentist is using the interproximal dental tool to grind between a patient's teeth, because the interproximal dental tool is slippery, it is possible that the dentist can lose his grip on the sides of the interproximal dental tool and the interproximal dental tool will fall out of the dentist's hands. If the interproximal dental tool falls on the floor, it is simply a matter of washing and sterilizing the interproximal dental tool before it is used again on the patient or taking a substitute interproximal dental tool and using it while the first dental tool is being washed and sterilized. However, if the dental tool slips out of the dentist's hands and in the opposite direction and falls into the patient's mouth, it could possibly fall into or down the patient's throat. With a sharp blade at the end, this could create some very serious medical hazards.

Therefore, a significant improvement of the present invention is the creation of a retaining strap retaining the interproximal dental tool around the practitioner's hands and/or wrist so that in the event the practitioner should lose his or her grip on the interproximal dental tool, the tool will still be retained because it is retained by the retaining strap which extends into and through the interproximal dental tool and then is retained around the practitioner's hands and/or wrist.

Figure 9:
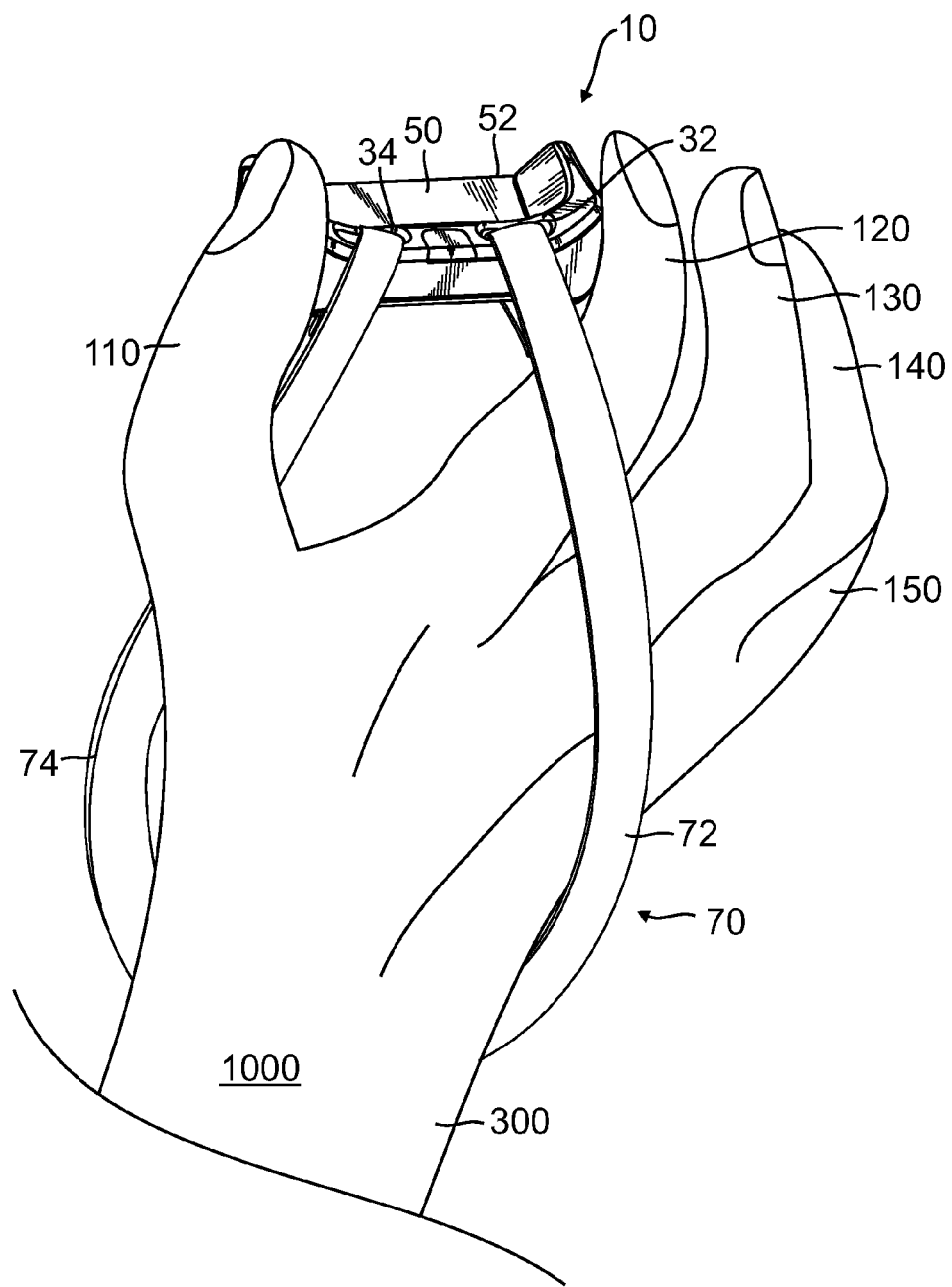
FIG. 9 is a perspective view of the present invention interproximal dental tool with a straight blade being held with a safety strap.

An illustration of the straight bladed apparatus with the present invention improvement is illustrated in FIG. 9. A portion of the practitioner's hand 1000 is illustrated in FIG. 9 which includes the practitioner's wrist 300 and the practitioner's fingers including the thumb 110, the forefinger 120, the middle finger 130, the fourth finger 140 an the pinkie finger 150. Most commonly the interproximal dental tool 10 is respectively gripped at its exterior sidewalls 22 and 26 and protrusions 24 and 28 between the thumb 110 and forefinger 120. The components of the interproximal dental tool 10 are as already stated. The addition is that there is a strap member 70 having a left section 74 and a right section 72. Section 72 extends through opening 32 and section 74 extends through opening 34. The two can either be tied at an end which is opposite the view from FIG. 9 or alternatively, can be one continuous strap which is then soldered together or thereafter molded together after the sections of strap are extended through the respective openings in the interproximal dental tool. As illustrated in FIG. 9, the practitioner grips the interproximal dental tool 10 primarily through the practitioner's thumb 110 and forefinger 120. For the sake of completeness, other fingers 130, 140 and pinkie finger 150 are also illustrated. The practitioner's wrist 300 is also illustrated. Other retaining members to retain the interproximal dental tool 10 around a practitioner's wrist are also within the spirit and scope of the present invention.

Figure 10:
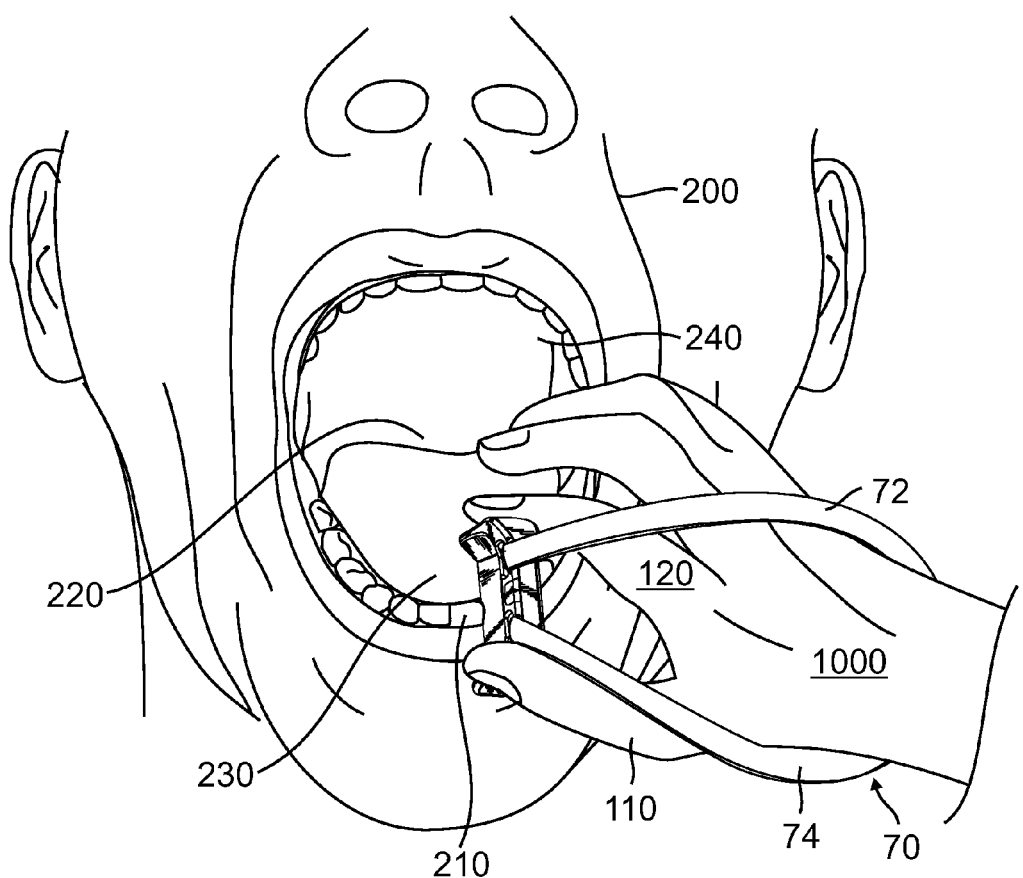
FIG. 10 is a perspective view of the present invention thereof in use by a dentist illustrating a person's mouth opened with the tool inserted between two adjacent teeth and held by a dentist or a dental hygienist.

Referring to FIG. 10, there is illustrated the straight interproximal dental tool 10 incorporating the present invention in use where a patient 200 has his mouth open where two of the patient's front teeth of which one 210 is shown and an adjacent tooth on the other side of the interproximal dental tool 10 which is not viewable in the view illustrated in FIG. 10. The interproximal dental tool 10 has its sharp razor edge 52 from razorblade 50 within the space between the two teeth and the dental practitioner is griping the sidewalls 22 and 26 between the practitioner's thumb and forefinger as illustrated in FIG. 10. Also illustrated is the patient's throat 220 and tongue 230. The practitioner is also using the retaining strap 70 as previously described which is affixed through the openings 32 and 34 in the interproximal dental tool and therefore the tool is now being operated where the practitioner is grinding between two teeth to remove a portion of the teeth at the location between the two teeth. As discussed, it is possible that the practitioner could lose the grip on the interproximal dental tool. The present invention has reduced that risk by incorporating the grippable top and sidewalls 20, 22 and 26 as already described and the protrusion members 24 and 28 which is the primary location where the dentist is respectively placing his or her thumb and forefinger. By way of example, the thumb is on exterior right sidewall 26 and is gripping the protrusions 28 while the forefinger is on the left sidewall 22 and is gripping the protrusions 24 to have a solid grip on the interproximal dental tool. Even with these improvements which are a substantial over the prior art hard plastic inventions which have a hard a top surface and sidewall and no protrusions, it is still possible that due to the wet environment in the patient's mouth, a dental practitioner can inadvertently lose his or her grip on the interproximal dental tool which, if it falls down the patient's throat 220, could create some serious problems.

Therefore, the present invention which further includes an interproximal dental tool retaining member such as a strap 70 which extends through openings 32 and 34 in the interproximal dental tool 10 and is either fixed or tied or is formed of one-piece construction which after passage through these openings is molded or welded or otherwise affixed together into a continuous strap which is wrapped around the practitioner's fingers and wrist so that should the practitioner lose the control of the interproximal dental tool 10 and fall away from the practitioner's fingers, the interproximal dental tool retaining member such as strap 70 will have the interproximal dental tool 10 simply fall away and dangle from the practitioner's hand or wrist and not fall down the patient's throat. Should the interproximal dental tool inadvertently fall into the patient's mouth 240 and even come close to the patient's throat 220, the practitioner can still pull the interproximal dental tool 10 away before it does any damage.

FIG. 11 illustrates the same variation except now using the arcuate design interproximal dental tool. The components are the same but are generally now arcuate in shape rather than straight in shape and also include an arcuate blade 50A with an arcuate sharp razor edge 52A which again is utilized and retained the same way as the straight embodiment where the arcuate interproximal dental tool 10A is gripped between the thumb 110 and forefinger 120 as previously described and is retained by the interproximal dental tool retaining member which is a strap that extends through openings 32A and 34A and also extends around the patient's fingers and wrist.

In FIG. 12 the arcuate interproximal dental tool 10A is shown in operation where the arcuate blade 50A is between two teeth of which one 210 is illustrated and again the grinding operation is performed. The key innovation is that the interproximal dental tool can be better gripped with the grippable top and sidewalls made of rubber or other grippable material and further is secured by the interproximal dental tool retaining member 70 which assures that the arcuate design interproximal dental tool 10A will not fall into the patient's mouth or down the patient's throat should the dental practitioner lose his or her grip on the interproximal dental tool.

Therefore, through the present invention the interproximal dental tool substantially includes the design of prior art interproximal dental tools in that the top section is retained with a rubber or grippable member which extends from the top to both sidewalls where each sidewall includes protrusions which further assist in gripping the interproximal dental tool by two fingers of the practitioner's hand which primarily are the thumb and forefinger and then having the interproximal dental tool retaining member which assures that should the dental practitioner lose his or her grip on the interproximal dental tool, the interproximal dental tool will not fall down a patient's throat but instead, will either be retrievable if it should fall into the patient's mouth or instead, will simply dangle from the interproximal dental tool retaining member and dangle below the practitioner's hand and wrist.

Therefore, the present invention makes the interproximal dental tool far safer and easier to operate and has a much improved design with improved elements to enable the practitioner to more securely grasp the interproximal dental tool and further assure that the interproximal dental tool will be retained should it slip out of the practitioners hand and will not fall down a patient's throat.

Of course the present invention is not intended to be restricted to any particular form or arrangement, or any specific embodiment, or any specific use, disclosed herein, since the same may be modified in various particulars or relations without departing from the spirit or scope of the claimed invention hereinabove shown and described of which the apparatus or method shown is intended only for illustration and disclosure of an operative embodiment and not to show all of the various forms or modifications in which this invention might be embodied or operated.

What is claimed is:

1. An interproximal dental tool, comprising:
   a. a left exterior surface made of grippable material extending to a top exterior surface made of grippable material extending to a right exterior surface made of grippable material, a rim including a left interior sidewall having a left front surface and a left back surface adjacent the left exterior surface, an interior top horizontal wall having a front top surface and a back top surface adjacent the top exterior surface, and a right interior sidewall having a right front surface and a right back surface adjacent the right exterior surface;
   b. a main body section having a transverse thickness and extending inward from the left interior sidewall and the left front surface and the left back surface of the left interior sidewall, and extending downward from the interior top horizontal wall and the front top surface and the back top surface of the interior top horizontal wall, and extending inward from the right interior sidewall and the right front surface and a right back surface of the right interior sidewall;
   c. a multiplicity of protrusions extending transverse to the left exterior surface and a multiplicity of protrusions extending transverse to the right exterior right surface;
   d. the interior top horizontal wall of the main body including a first opening which extends through an entire thickness of the interior top horizontal wall from the front top surface to the back top surface and a spaced apart second opening which extends through the entire thickness of the interior top horizontal wall from the front top surface to the back top surface;
   e. a main razorblade retaining section surrounded by the main body section, the main razorblade retaining section including a left interior sidewall extending to an interior horizontal wall extending to a right interior sidewall;
   f. a razorblade retaining slot within the left interior sidewall and the interior horizontal wall and the right interior sidewall of the main razorblade retaining section with a razorblade retained within the razorblade retaining slot, the razorblade having a bottom exposed sharp edge; and
   g. a retaining strap having a first end extending through the first opening in the interior top horizontal wall from the front top surface of the interior top horizontal wall through the back top surface of the interior top horizontal wall, the retaining strap having a second end extending through the second opening in the interior top horizontal wall from the front top surface of the interior top horizontal wall through the back top surface of the interior top horizontal wall, the first and second ends of the retaining strap retained together, the retaining strap having a length of strap material between the first end and the second end of the retaining strap, the length of strap hanging from the interior top horizontal wall of the main body.

2. The interproximal dental tool in accordance with claim 1, wherein the left exterior surface, the top exterior surface, the right exterior surface, the rim, the main body section, the main razorblade retaining section, the razorblade retaining slot and the razorblade are aligned in a straight configuration.

3. The interproximal dental tool in accordance with claim 1 wherein the left exterior surface, the top exterior surface, the right exterior surface, the rim, the main body section, the main razorblade retaining section, the razorblade retaining slot and the razorblade are aligned in an arcuate configuration.

4. The interproximal dental tool in accordance with claim 1, where the grippable material of the left exterior surface, the top exterior surface and the right exterior surface is rubber.

5. An interproximal dental tool, comprising:
   a. a left exterior surface made of grippable material extending to a top exterior surface extending to a right exterior surface made of grippable material, a rim including a left interior sidewall having a left front surface and a left back surface adjacent the left exterior surface, an interior top horizontal wall having a front top surface and a back top surface adjacent the top exterior surface, and a right interior sidewall having a right front surface and a right back surface adjacent the right exterior surface;
   b. a main body section having a transverse thickness and extending inward from the left interior sidewall and the left front surface and the left back surface of the left interior sidewall, and extending downward from the interior top horizontal wall and the front top surface and the back top surface of the interior top horizontal wall, and extending inward from the right interior sidewall and the right front surface and a right back surface of the right interior sidewall;
   c. a multiplicity of protrusions extending transverse to the left exterior surface and a multiplicity of protrusions extending transverse to the right exterior right surface;
   d. the interior top horizontal wall of the main body including a first opening which extends through an entire thickness of the interior top horizontal wall from the front top surface to the back top surface and a spaced apart second opening which extends through the entire thickness of the interior top horizontal wall from the front top surface to the back top surface;
   e. a main razorblade retaining section surrounded by the main body section, the main razorblade retaining section including a left interior sidewall extending to an interior horizontal wall extending to a right interior sidewall;
   f. a razorblade retaining slot within the left interior sidewall and the interior horizontal wall and the right interior sidewall of the main razorblade retaining section with a razorblade retained within the razorblade retaining slot, the razorblade having a bottom exposed sharp edge; and
   g. a retaining strap having a first end, a second end and a length of strap material between the first end and the second end, the retaining strap retained together at the first end and the second end adjacent one surface of the interior top horizontal wall of the main body after having the first end pass through the first opening in the interior top horizontal wall and having the second end pass through the second opening in the interior top horizontal wall, the length of strap material hanging from an opposite surface of the interior top horizontal wall of the main body.

6. The interproximal dental tool in accordance with claim 5, wherein the left exterior surface, the top exterior surface, the right exterior surface, the rim, the main body section, the main razorblade retaining section, the razorblade retaining slot and the razorblade are aligned in a straight configuration.

7. The interproximal dental tool in accordance with claim 5 wherein the left exterior surface, the top exterior surface, the right exterior surface, the rim, the main body section, the main razorblade retaining section, the razorblade retaining slot and the razorblade are aligned in an arcuate configuration.

8. The interproximal dental tool in accordance with claim 5, where the grippable material of the left exterior surface, the top exterior surface and the right exterior surface is rubber.

9. An interproximal dental tool, comprising:
   a. a left exterior surface made of grippable material extending to a top exterior surface extending to a right exterior surface made of grippable material, a rim including a left interior sidewall having a left front surface and a left back surface adjacent the left exterior surface, an interior top horizontal wall having a front top surface and a back top surface adjacent the top exterior surface, and a right interior sidewall having a right front surface and a right back surface adjacent the right exterior surface;
   b. a main body section having a transverse thickness and extending inward from the left interior sidewall and the left front surface and the left back surface of the left interior sidewall, and extending downward from the interior top horizontal wall and the front top surface and the back top surface of the interior top horizontal wall, and extending inward from the right interior sidewall and the right front surface and a right back surface of the right interior sidewall;
   c. a multiplicity of protrusions extending transverse to the left exterior surface and a multiplicity of protrusions extending transverse to the right exterior right surface;
   d. the interior top horizontal wall of the main body including a first opening which extends through an entire thickness of the interior top horizontal wall from the front top surface to the back top surface and a spaced apart second opening which extends through the entire thickness of the interior top horizontal wall from the front top surface to the back top surface;
   e. a main razorblade retaining section surrounded by the main body section, the main razorblade retaining section including a left interior sidewall extending to an interior horizontal wall extending to a right interior sidewall;
   f. a razorblade retaining slot within the left interior sidewall and the interior horizontal wall and the right interior sidewall of the main razorblade retaining section with a razorblade retained within the razorblade retaining slot, the razorblade having a bottom exposed sharp edge; and
   g. a retaining strap extending through the first opening and the second opening in the interior top horizontal wall and affixed at a location adjacent one side of the interior top horizontal wall and having a length of strap hanging from a location adjacent an opposite side of the interior top horizontal wall.

10. The interproximal dental tool in accordance with claim 9 further comprising: the retaining strap having a first end extending through the first opening in the interior top horizontal wall from the front top surface of the interior top horizontal wall through the back top surface of the interior top horizontal wall, the retaining strap having a second end extending through the second opening in the interior top horizontal wall from the front top surface of the interior top horizontal wall through the back top surface of the interior top horizontal wall, the first and second ends of the retaining strap retained together, the retaining strap having a length of strap material between the first end and the second end of the retaining strap, the length of strap hanging from the interior top horizontal wall of the main body.

11. The interproximal dental tool in accordance with claim 9 further comprising: the retaining strap having a first end, a second end and a length of strap material between the first end and the second end, the retaining strap retained together at the first end and the second end adjacent one surface of the interior top horizontal wall of the main body after having the first end pass through the first opening in the interior top horizontal wall and having the second end pass through the second opening in the interior top horizontal wall, the length of strap material hanging from an opposite surface of the interior top horizontal wall of the main body.

12. The interproximal dental tool in accordance with claim 9, wherein the left exterior surface, the top exterior surface, the right exterior surface, the rim, the main body section, the main razorblade retaining section, the razorblade retaining slot and the razorblade are aligned in a straight configuration.

13. The interproximal dental tool in accordance with claim 9 wherein the left exterior surface, the top exterior surface, the right exterior surface, the rim, the main body section, the main razorblade retaining section, the razorblade retaining slot and the razorblade are aligned in an arcuate configuration.

14. The interproximal dental tool in accordance with claim 9, where the grippable material of the left exterior surface, the top exterior surface and the right exterior surface is rubber.

* * * * *

UNITED STATES PATENT AND TRADEMARK OFFICE
CERTIFICATE OF CORRECTION

PATENT NO.         : 9,277,975 B1                                              Page 1 of 1
APPLICATION NO.    : 14/523910
DATED              : March 8, 2016
INVENTOR(S)        : Bryan Tapocik It is certified that error appears in the above-identified patent and that said Letters Patent is hereby corrected as shown below:

In the Specification:

In Col. 3, line 60, "in addition to" should read --In addition to--.

In Col. 4, line 53, "bottom sham edge" should read --bottom sharp edge--.

In Col. 5, line 17, "an the pinkie finger" should read --and the pinkie finger--.

In Col. 5, line 65, "which are a substantial" should read --which are substantial--.

In Col. 5, line 66, "which have a hard a top surface" should read --which have a hard top surface--.

In the Claims:

In Col. 7, line 34, Claim 1, "the right exterior right surface;" should read --the right exterior surface;--.

In Col. 8, line 32, Claim 5, "the right exterior right surface;" should read --the right exterior surface;--.

In Col. 9, line 27, Claim 9, "the right exterior right surface;" should read --the right exterior surface;--.

Signed and Sealed this
Fourteenth Day of June, 2016

Michelle K. Lee
*Director of the United States Patent and Trademark Office*